United States Patent
Patel et al.

(10) Patent No.: US 7,060,739 B2
(45) Date of Patent: *Jun. 13, 2006

(54) ANTIMICROBIAL FLUOROELASTOMER RUBBER ARTICLES AND COMPOSITIONS

(75) Inventors: Bhawan Patel, Bolton (GB); David L. Morris, Manchester (GB)

(73) Assignee: Milliken & Company, Spartanburg, SC (US)

( * ) Notice: Subject to any disclaimer, the term of this patent is extended or adjusted under 35 U.S.C. 154(b) by 181 days.

This patent is subject to a terminal disclaimer.

(21) Appl. No.: 10/424,024

(22) Filed: Apr. 25, 2003

(65) Prior Publication Data

US 2004/0214916 A1   Oct. 28, 2004

(51) Int. Cl.
*C08K 3/08* (2006.01)
*C08K 3/10* (2006.01)
*C08K 3/34* (2006.01)
*C08K 5/09* (2006.01)

(52) U.S. Cl. .................. 523/122; 524/86; 524/287; 524/297; 524/398; 524/403; 524/450; 524/492

(58) Field of Classification Search ............... 523/122; 524/86, 287, 297, 398, 403, 450, 492
See application file for complete search history.

(56) References Cited

U.S. PATENT DOCUMENTS

| 5,441,717 | A | 8/1995 | Ohsumi et al. ............. 423/306 |
| 5,466,726 | A | 11/1995 | Inoue et al. ................ 523/122 |
| 5,698,229 | A | 12/1997 | Ohsumi et al. ............. 424/604 |
| 5,736,591 | A | 4/1998 | Dunn ........................ 523/122 |
| 6,448,306 | B1 * | 9/2002 | Lever et al. ................ 523/122 |
| 6,455,610 | B1 * | 9/2002 | Lever et al. ................ 523/122 |
| 6,555,599 | B1 | 4/2003 | Lever et al. ................ 523/122 |
| 6,846,871 | B1 * | 1/2005 | Patel et al. ................. 524/440 |

FOREIGN PATENT DOCUMENTS

| JP | 7194661 | 12/1993 |
| JP | 1993000355168 | 12/1993 |
| JP | 8239577 | 2/1995 |
| JP | 1995000038991 | 2/1995 |
| JP | 1995000065149 | 2/1995 |
| JP | 1997000026273 | 2/1997 |
| JP | 1997000140034 | 5/1997 |
| JP | 1997000342076 | 11/1997 |

* cited by examiner

*Primary Examiner*—Kriellion A. Sanders
(74) *Attorney, Agent, or Firm*—Terry T. Moyer; Brenda D. Wentz

(57) ABSTRACT

Fluoroelastomer (FKM) rubber-containing articles that exhibit highly desirable long-term effective antimicrobial characteristics are provided. Such articles are in either solid or blown (foam or sponge) state (or combinations of both in multilayered forms) and can be utilized in a variety of applications. This invention utilizes the presence of non-sulfur-based curing systems and agents, such as bisphenols, that permit vulcanization and do not irreversibly bind silver ions thereto, thereby resulting in long-term antimicrobial performance of the rubber article. This invention further provides a simple method of producing such an antimicrobial vulcanized fluoroelastomer rubber-containing article. This invention also encompasses certain non-silicone pre-vulcanized raw rubber formulations made from at least a majority by weight of FKM rubber that include silver-based components to provide highly desirable long-term antimicrobial characteristics within the ultimate cured FKM articles made therefrom.

21 Claims, No Drawings

ANTIMICROBIAL FLUOROELASTOMER RUBBER ARTICLES AND COMPOSITIONS

FIELD OF THE INVENTION

This invention relates to certain non-silicone vulcanized rubber articles made from at least a majority by weight of fluoroelastomer rubber (FKM) that include silver-based compounds to provide highly desirable long-term antimicrobial characteristics within the cured rubber articles. Such articles are in either solid or blown (foam or sponge) state (or combinations of both in multilayered forms) and can be utilized in a variety of different applications.

As silver-based compounds are deleteriously affected by utilization of standard curing agents and curing accelerators, such as sulfur-based compounds and/or systems, the ability to provide such an effective antimicrobial vulcanized rubber article is rather difficult. However, this invention encompasses the presence of different non-sulfur-based curing systems and agents, such as bisphenol and peroxide, as examples, that permit vulcanization and do not irreversibly bind silver ions thereto, thereby resulting in long-term antimicrobial performance of the ultimate rubber article itself. This invention also encompasses a simple method of producing such an antimicrobial vulcanized fluoroelastomer rubber-containing article. Furthermore, this invention provides certain non-silicone pre-vulcanized raw rubber formulations made from at least a majority by weight of FKM rubber that include silver-based components to provide highly desirable long-term antimicrobial characteristics within the ultimate cured FKM articles made therefrom.

DISCUSSION OF THE PRIOR ART

All U.S. Patents listed below are herein entirely incorporated by reference.

There has been a great deal of attention in recent years given to the hazards of bacterial contamination from potential everyday exposure. Noteworthy examples of such concerns include the fatal consequences of food poisoning due to certain strains of *Escherichia coli* being found within undercooked beef in fast food restaurants; *Salmonella enteritidis* contamination causing sicknesses from undercooked and unwashed poultry food products; and illnesses and skin infections attributed to *Staphylococcus aureus, Klebsiella pneumoniae,* yeast (*Candida albicans*), and other unicellular organisms. With such an increased consumer interest in this area, manufacturers have begun introducing antimicrobial agents within various everyday products and articles. For instance, certain brands of cutting boards, shoe soles, shoe inserts, medical devices and implements, liquid soaps, etc., all contain antimicrobial compounds. The most popular antimicrobial for such articles is triclosan. Although the incorporation of such a compound within liquid or certain polymeric media has been relatively simple, other substrates, specifically vulcanized rubber and surfaces thereof, have proven less accessible. Furthermore, such triclosan additives have proven to be difficult in use or ineffective for certain bacteria. For instance, triclosan itself migrates easily within and out of certain polymeric substrates and/or matrices (and thus is not very durable), lacks thermal stability (and thus readily leaches out of rubber and like materials at higher temperatures), and does not provide a wide range of bacterial kill (for instance, does not exhibit any kill for *Pseudomonas aeruginosa*).

Antimicrobial rubber formulations are certainly highly desired for the production of vulcanized rubber articles and compositions to provide not only antibacterial benefits, but also antifungal, antimildew, antistaining, and odor control properties. Rubber articles are utilized in many different applications, from automobiles (hoses, tires, bumpers, etc.), to household items (toys, sink washers, gaskets, appliances, floor mats, door mats, carpeted rubber mats, gloves, and the like), and other areas in which bacterial growth is a potential problem. Thus, there remains a long-felt need to provide an effective, durable, reliable antimicrobial pre-vulcanized rubber formulation which will provide such long-term antimicrobial, antifungal, etc., effects within the final vulcanized article. Unfortunately, such a highly desired antimicrobial rubber formulation and/or vulcanized article containing silver-based antimicrobial agents has heretofore not been provided by the pertinent prior art.

The closest art includes Japanese Patent Application 1997-342076 which discloses the production of unvulcanized rubber formulations and articles exhibiting antibacterial properties due to the presence of silver complexes. Such formulations are formed through high temperature kneading in an oxygen-free atmosphere and are used as parts in a water disinfection system. Again, no vulcanized rubber is taught or obtained within or through this disclosure.

Antimicrobial rubber bands have been taught in Japanese Patent Application 1997-140034 in vulcanized form with silver antimicrobials therein. However, such compounds are rather limited in use and the vulcanization step must include a sulfur curing agent to effectuate the final vulcanized arrangement of the subject rubber. Such sulfur curing agents have a remarkably deleterious effect on certain silver-based antimicrobials such that the sulfur reacts with the silver ion to from silver sulfide, thereby rendering it ineffective as a bactericide. As such, the utilization of such specific rubber band formulations for and within large-scale antimicrobial articles is basically unworkable.

Certain types of antimicrobial peroxide-catalyst vulcanized rubber formulations have been produced in the past; however, such peroxide-cured rubbers are all silicone-based. It is well understood and accepted that silicone rubbers cannot be vulcanized by typical sulfur-based catalysts. Thus, the antimicrobial rubber formulations of Japanese Patent Applications 1997-026273 and 1995-065149 as well as U.S. Pat. No. 5,466,726 are standard vulcanized silicone rubber formulations and articles which also include certain antimicrobial compounds. Additionally, some types of rubber, such as butyl and its derivative chlorobutyl rubber, have a tendency to de-polymerize when cured with peroxide based curing systems.

Furthermore, rubber latexes (non-vulcanized) comprising antimicrobials have been disclosed (U.S. Pat. No. 5,736,591, for example), as have floor mats having silver-based antimicrobials incorporated within pile fiber components. These floor mats have non-antimicrobial rubber backings cured through peroxide-catalyzed vulcanization to protect the pile fiber antimicrobial compounds from attack by any sulfur compounds (as in Japanese Patent Applications 1993-3555168 and 1995-38991). Again, however, to date there have been no disclosures or suggestions of producing a vulcanized FKM rubber formulation or article exhibiting excellent antimicrobial properties through the long-term effective utilization of silver-based antibacterial compounds. This invention fills such a void.

OBJECT OF THE INVENTION

It is therefore an object of this invention to provide an antimicrobial vulcanized fluoroelastomer rubber-containing article exhibiting sufficient antimicrobial activity and structural integrity to withstand repeated use without losing an appreciable level of either antimicrobial power or modulus strength. Another object of the invention is to provide an antimicrobial vulcanized fluoroelastomer rubber article comprising silver-based antimicrobial compounds which include curing agents that do not deleteriously effect the antimicrobial activity of the finished vulcanized fluoroelastomer article (and thus is essentially free from sulfur-based curing agents and accelerators). Yet another object of this invention is to provide a vulcanized fluoroelastomer rubber-containing article that exhibits silver elution at a rate of a least 1.5 ng/cm$^2$ after 24 hours exposure at room temperature. Still another object of this invention is to provide a simple method of producing such an antimicrobial vulcanized fluoroelastomer rubber-containing article.

A further object of this invention is to provide an antimicrobial substantially FKM pre-vulcanized raw rubber formulation that ultimately provides a vulcanized FKM rubber article of sufficient antimicrobial activity and structural integrity to withstand repeated use without losing an appreciable level of either antimicrobial efficiency or modulus strength. Another object of this invention is to ultimately provide an antimicrobial FKM pre-vulcanized rubber formulation comprising silver-based antimicrobial compounds which include curing agents and curing accelerators which do not deleteriously effect the antimicrobial activity of the ultimate vulcanized FKM rubber article (and thus is essentially free from sulfur-based curing agents and accelerators). Yet another object of this invention is to provide an unvulcanized FKM raw rubber formulation that, upon vulcanization, cures to form such an antimicrobial FKM vulcanized rubber article exhibiting silver elution at a rate of at least 1.5 ng/cm$^2$ after 24 hours exposure at room temperature.

Accordingly, this invention encompasses a dimensionally stable vulcanized fluoroelastomer rubber-containing article exhibiting silver elution at a rate of at least 1.5 ng/cm$^2$ after 24 hours exposure at room temperature. Furthermore, this invention encompasses such a vulcanized fluoroelastomer rubber-containing article comprising at least one silver ion control release additive, such as those selected from the group consisting of fillers (such as carbon black, magnesium oxide, calcium hydroxide, calcium carbonate, inorganic salts, organic salts, silica, and mixtures thereof) and plasticizers (oils such as phthalate oils and paraffinic oils). Additionally, this invention encompasses a method of producing a vulcanized fluoroelastomer rubber-containing article comprising the steps of providing a rubber formulation of uncured rubber, at least one non-sulfur based curing agent, and at least one silver-based antimicrobial compound, and vulcanizing said rubber formulation at a temperature of at least 150° C. and at least at a pressure of 3 bars, wherein said rubber formulation is substantially free from sulfur curing agent and accelerator. This invention also encompasses a pre-vulcanized rubber formulation comprising at least one rubber constituent, the majority of which must be fluoroelastomer rubber, at least one silver-based antimicrobial compound and at least one curing compound, wherein all of said curing compounds present within said formulation does not include an appreciable amount of sulfur-based compounds, and wherein said rubber formulation optionally comprises at least one silver ion release control additive.

DETAILED DESCRIPTION OF THE INVENTION

The term "dimensionally stable" is intended to encompass a vulcanized rubber article that is structurally able to be handled without disintegrating into smaller portions. Thus, the article must exhibit some degree of structural integrity and, being a rubber, a certain degree of flexural modulus.

Such a specific antimicrobial vulcanized fluoroelastomer rubber-containing article has not been taught nor fairly suggested within the rubber industry or prior art. As noted above, the avoidance of sulfur-based curing agents and accelerators to any appreciable degree thus permits the retention of silver antimicrobials within the final product in amounts sufficient to provide long-lasting log kill rates for *Staphylococcus aureus, Klebsiella pneumoniae, Pseudomonas aeruginosa,* and *Escherichia coli,* at the very least. Furthermore, due primarily to high costs, non-sulfur curing agents have not been prevalent within vulcanized rubber formulations and articles. As such, there has been no teaching or fair suggestion of coupling non-sulfur curing agents (and most preferably bisphenol curing agents) with silver-based antimicrobial agents within pre-vulcanized fluoroelastomer rubber formulations to form effectively antimicrobial vulcanized rubber articles.

Additionally, certain fillers and oils (such as silica, carbon black, magnesium oxide, calcium hydroxide, stearates as fillers, and phthalate and paraffinic oils) are generally, although not necessarily, required to provide both flexural modulus and structural integrity to vulcanized rubber articles. The rubber component alone generally does not exhibit proper dimensional stability without such additives. The presence of such additives may also provide the ability to control silver-ion release at the target article surface. Without intending to be bound to any specific scientific theory, it appears that such fillers as silica and such oils as paraffinic oil (as some examples), act in such a way as to draw moisture into the article which then transports silver ions from within the article to the surface. In such a situation, then, the rubber article may exhibit enhanced silver release resulting in higher log kill rates for certain bacteria due to the presence of larger amounts of available surface silver ions.

Other hydrophobic fillers, such as pigments (for example, carbon black) and calcium carbonate appear to work in the opposite manner by keeping water out of the target article and prevent silver-ion migration to the article surface. Thus, the reduction of such silver-ion availability decreases the antibacterial efficacy of the rubber article. In effect, then, the actual antibacterial efficacy of the entire rubber article can be controlled through the presence of certain amounts of such generally required fillers and oils (some hydrophilic antistatic agents also appear to act in the same manner as silica as well).

As a result, the necessary filler and/or oil constituents required to provide dimensional resiliency and/or flexural modulus (and thus actual usefulness) of the finished article serve a dual purpose heretofore unrecognized within the rubber industry. Rubber articles can be produced with specific end-uses in mind depending upon the duration of antimicrobial activity desired through the addition of specific amounts of such additives. Again, such a targeted duration antimicrobial vulcanized article and the benefits thereof have heretofore been unknown and unrecognized within the rubber industry. These rubber components are thus hereinafter referred to as "silver ion release control additives".

The term fluoroelastomer rubber, as noted above, is intended to cover any standard rubber which possesses at least a majority by weight of fluoroelastomer rubber and which must be vulcanized to provide a dimensionally stable rubber article. Fluoroelastomer rubber is generically referred to as FKM polymer according to the nomenclature noted in ASTM D1418 and is often classified by its fluorine content. For example, many standard fluoroelastomer rubbers are available having a fluorine content of 66%, 68%, and 70%, although many specialty grades are now available with fluorine content in a range of between about 60% and about 75%.

It is intended that vulcanization or other processing of the fluoroelastomer rubber be performed in an environment that is inexpensive to provide and should be undertaken in an oxygen-rich atmosphere (as opposed to an anaerobic environment which is generally difficult to provide). Fluoroelastomer rubber has been utilized previously within the rubber industry for a variety of applications and is generally well known and taught throughout the prior art. Such inventive rubber articles may also possess a chemical plasticizer which aids in the breakdown period of the elastomer during compounding and processing (and provides flexural modulus properties to the finished article) as well as fillers required for reinforcement (e.g. calcium carbonate, carbon black, magnesium oxide, calcium hydroxide, silica, and clays). Optionally, to form a blown (foam or sponge) rubber article, a blowing agent may be added to the inventive formulation.

The non-silicone rubber component or components of the inventive rubber article is therefore comprised of a majority of fluoroelastomer rubber. Other types of rubber may be combined with the fluoroelastomer rubber (in order to provide different strengths, flexibilities, or other properties) such as those selected from the group consisting of nitrile rubber [such as acrylonitrile-butadiene rubber (NBR)], styrene-butadiene rubber (SBR), natural rubber, chloroprene rubber, ethylene propylene rubber, ethylene propylene diene monomer (EPDM) rubber, natural rubber, polyurethane rubber, butyl rubber, isoprene rubber, halobutyl rubber, epichlorohydrin rubber, polyacrylate rubber, chlorinated polyethylene rubber, hydrogenated NBR, carboxylated NBR, polybutadiene rubber, and the like. Although the presence of silicone rubber is discouraged within the inventive formulation, there remains the possibility of adding certain low amounts of such specific unvulcanized rubber components without adversely affecting the overall antimicrobial rubber formulation itself. Thus, up to 25% by total weight of the formulation may be silicone rubber; however, the vast majority of the rubber formulation must be non-silicone rubber, and in particular, fluoroelastomer rubber.

Furthermore, the non-silicone rubber portion must not possess an appreciable amount of sulfur-based curing agent or residue (in the finished article) and thus must be vulcanized through curing with primarily non-sulfur-based compounds (such as bisphenols, peroxides, and metal oxides, for example). The rubber component is present in an amount of from about 10 to about 1,000 parts of the entire composition, more preferably-from about 50 to about 500 parts, and most preferably from about 70 to about 200 parts of the entire composition. Thus, with a total number of parts between about 100 and about 2,000 parts throughout the target vulcanized rubber article, the rubber constitutes from about 25 to about 70% of the percentage by parts of the entire article. The remainder comprises additives such as fillers, oils, curing agents, the desired antimicrobial agents, optional blowing agents, and the like (as discussed more thoroughly below).

The antimicrobial agent of the inventive raw rubber formulation may be of any standard silver-based compounds. Such compounds, in contrast with organic types, such as triclosan, for example, do not exhibit low thermal stability and remain within the target matrix or substrate at different temperatures. Thus, such an antimicrobial is more easily controlled, as discussed above, for surface-release as desired. Such agents include, without limitation, silver salts, silver oxides, elemental silver, and, most preferably, ion exchange, glass, and/or zeolite compounds. Of even greater preference are silver-based ion exchange compounds for this purpose due to the low levels of discoloration and enhanced durability in the final product provided by such compounds, the efficacy provided to the final formulation with such a compound, and the ease of manufacture permitted with such specific compounds. Thus, the antimicrobial agent of this invention may be any type which imparts the desired log kill rates to *Staphylococcus aureus, Klebsiella pneumoniae, Escherichia coli,* and *Pseudomonas aeruginosa,* as merely representative organisms. Furthermore, such antimicrobial compounds must be able to withstand elevated processing temperatures for successful incorporation within the target non-sulfur (bisphenol, for example) cured fluoroelastomer rubber-containing articles. Again, such antimicrobial agents comprise, preferably, silver-containing ion exchange, glass, and/or zeolite compounds. Most preferably, such a compound is a silver-based ion-exchange compound and particularly does not include any added organic bactericide compounds (thereby not permitting a release of volatile organic compounds into the atmosphere during processing at high temperatures, etc.).

The preferred silver-based ion exchange material is an antimicrobial silver zirconium phosphate available from Milliken & Company, under the trade name ALPHASAN®. Such compounds are available in different silver ion concentrations as well as mixtures with zinc oxide. Thus, different compounds of from about 0.01 to 15% of silver ion concentration, more preferably from about 3 to about 10%, and most preferably amounts of about 10% by total amount of components (e.g. of the total amount of silver ions and zirconium phosphate) are possible. Other potentially preferred silver-containing solid inorganic antimicrobials in this invention are silver-substituted zeolite available from Sinanen under the tradename ZEOMIC®, or a silver-substituted glass available from Ishizuka Glass under the tradename IONPURE®, which may be utilized either in addition to or as a substitute for the preferred species. Other possible compounds, again without limitation, are silver-based materials such as MICROFREE®, available from DuPont, as well as JMAC®, available from Johnson Mathey.

Generally, such an antimicrobial compound is added to a rubber formulation in an amount of from about 0.1 to 10% by total weight of the particular total rubber formulation, preferably from about 0.1 to about 5%, more preferably from about 0.1 to about 2%, and most preferably about 2%.

Furthermore, with regard to silver-based inorganic antimicrobial materials, these particular antimicrobial rubber articles are shown to be particularly suitable for the desired high levels of efficacy and durability required of such articles. It has been found that certain silver-based ion exchange compounds, such as ALPHASAN® brand antimicrobials available from Milliken & Company, (U.S. Pat. No. 5,926,238, U.S. Pat. No. 5,441,717, U.S. Pat. No. 5,698,229 to Toagosei Chemical Industry Inc.), exhibit impressive bio-efficacy. After a period of time, alternative antimicrobial compounds (e.g. triclosan, microchek, OBPA, Zn-omadine) initially suffer from decomposition under the high processing temperatures, which is followed by depletion of the biocide through leaching into the surrounding environment and finally through depleted bactericidal activity. However, silver-containing ion exchange, glass, and/or zeolite compounds do not suffer from these shortcomings. Such antimicrobial agents exhibit high temperature stability (>1000° C.), do not leach into the environment and provide substantial amounts of the oligodynamic silver ion to provide for the desired extensive durability.

In testing the antimicrobial rubber articles for effectiveness, it has been generally observed that a relationship exists between silver elution values (quantity of silver ions released at the surface of the article) and antimicrobial efficacy against certain organisms. For example, silver elution values greater than about 1.5 $ng/cm^2$ silver generally result in the maximum log kill reduction against *Klebsiella pneumoniae* and *Staphylococcus aureus*. Accordingly, it is generally desirable that the inventive antimicrobial articles should exhibit an acceptable log kill rate after 24 hours for *S. aureus* when tested in accordance with the ATCC Test Method 6538 and for *K. pneumoniae* when tested in accordance with ATCC Test Method 4352. Such an acceptable level log kill rate is tested for *S. aureus* or *K. pneumoniae* of at least 0.1 increase over baseline. Alternatively, an acceptable level will exist if the log kill rate is greater than the log kill rate for non-treated (i.e., no solid inorganic antimicrobial added) rubber articles (such as about 0.5 log kill rate increase over control, antimicrobial-free vulcanized rubber article). Preferably, these log kill rate baseline increases are at least 0.3 and 0.3, respectively for *S. aureus* and *K. pneumoniae;* more preferably these log kill rates are 0.5 and 0.5, respectively; and most preferably these are 1.0 and 1.0, respectively. Of course, the high end of such log kill rates are much higher than the baseline, on the magnitude of 5.0 (99.999% kill rate). Any rate in between is thus, of course, acceptable as well.

However, log kill rates which are negative in number are also acceptable for this invention as long as such measurements are better than that recorded for correlated non-treated rubber articles. In such an instance, the antimicrobial material present within the rubber article at least exhibits a hindrance to microbe growth. Furthermore, such rubber articles should exhibit log kill rates of the same degree for other types of bacteria, such as, *Pseudomonas aeruginosa* and *Escherichia coli*.

It is also contemplated within this invention that the sulfinished inventive articles will provide antifungal benefits as well as antibacterial characteristics. Such versatility is rare among antibacterial compounds; however, without intending to be limited to any particular scientific theory, it appears that the silver ions, and particularly the silver ions present at the article surface in great abundance, provide excellent antifungal properties. For example, it is believed that this inventive rubber formulation should provide fungal kill durability of at least 15 sequential days for such organisms as *Aspergillus niger* and possibly for mixtures of fungi including *A. niger* ATCC 6275, *Paecilomyces variotii* ATCC 18502, and *Trichoderma virens* ATCC 9645, when tested according to Test Method ISO 846. In order to provide a greater array of potential antifungal benefits, other compounds may be incorporated within the target pre-vulcanized rubber formulation (and subsequent article), such as zinc oxide, as one example.

Of great importance to the effectiveness of the inventive articles in terms of antimicrobial and antifungal activity is the omission of deleterious amounts of sulfur-based curing agents, accelerators, and additives which bind silver (such as barium sulfate filler used in non-black FKM rubber) from the rubber article. As noted above, it is believed, without intending to be bound to any specific scientific theory, that sulfur reacts with the preferred silver-based antimicrobials and irreversibly binds the silver ions (as silver sulfides, for example) within the rubber composition and/or article itself. As such, the resultant silver sulfides, etc., are ineffective as antimicrobial agents and their presence renders the final product antimicrobially inactive. Thus, it has been necessary to produce a vulcanized rubber article lacking any appreciable amount of sulfur curing agents, accelerators, and additives therein. It should be appreciated that the term "appreciable amount" permits a small amount to be present. It has been found that, as a molar ratio, a 1:1 ratio (and above) between sulfur molar presence and silver molar presence results in a clear loss of antimicrobial activity within the desired ultimate vulcanized article. However, greater molar amounts of silver in relation to sulfur provide at least some antimicrobial properties to the desired article. A molar ratio range of from about 0.25:1 to about 0.000000001:1 of sulfur to silver ions is thus at least acceptable. The primary curing agent, however, must be of non-sulfur nature (and is preferably, though not necessarily, a bisphenol-based compound) in order to provide the desired antimicrobial activity for the subject rubber.

Although bisphenol curing agents have been utilized for vulcanization of rubber previously, such a different type of curing agent is not widely utilized as a suitable vulcanization catalyst for rubber for a number of reasons. Foremost, such curing agents are much more costly than standard sulfur-based agents and the utilization of such bisphenols, and the like, as a replacement for the sulfur-based compounds have been rather limited to mostly silicone-based rubbers or, at the very least, non-antibacterial rubber articles. However, due to the problems associated with antimicrobial activity when such compounds are reacted with sulfur-based curing agents, alternatives to such sulfur-based cured articles was to permit utilization of such effective antimicrobial compounds within raw and vulcanized rubber for long-term high log kill rate effects. Thus, although non-sulfur-based compounds are not readily utilized within the non-silicone industry as vulcanization curing agents, utilization of such curing agents was necessary to provide an effective, ultimate antimicrobial vulcanized rubber article.

Surprisingly, it has now been found that the inventive rubber articles listed above are available without such sulfur-based curing agents in any appreciable amounts; most importantly, with the introduction of certain additives, the structural integrity and/or flexural modulus of the rubber formulation is improved to an acceptable level, and the efficacy of the antimicrobial components can be controlled simultaneously.

Thus, the curing agent present within the raw rubber formulation to be vulcanized to form the inventive article must be at least a majority, and preferably at least about 75% by weight of a non-sulfur-based curing agent. As discussed above, traditional sulfur and sulfur-based catalysts will not work with the inventive antimicrobial formulations due to chemical reactions between the sulfur atoms and the biocidal Ag+ ion. However, non-sulfur-based catalysts provide effective curing for the inventive raw rubber formulations, such as, for example and without limitation, bisphenols, peroxides, and oxides. Peroxides include, for example, organic peroxides such as dicumyl peroxide, 2,5-bis(t-butylperoxy)-2,5-dimethylhexane, di-(t-butyl-peroxy-isopropyl) benzene, di-(t-butyl-peroxy-trimethyl)-cyclohexane, and the like, as well as inorganic peroxides. Oxides include, for example, zinc oxide, and the like. Some curing agents, bisphenol for example, may already be incorporated in the unvulcanized rubber during the manufacturing process. These curing agents should generally be present in amount of from about 0.5 to about 100 parts per hundred parts of rubber (pphr), more preferably from about 1 to about 50 pphr, and most preferably from about 1 to about 10 pphr, all either as one curing agent alone, or as the combination of any number of different types of curing agents.

Other additives present within the inventive vulcanized rubber article may include any of the aforementioned silver ion release control additives, accelerators, accelerator activators, antidegradants, softeners, abrasives, colorants, flame retardants, homogenizing agents, internal lubricants, and deodorants. Such components should be present, if at all, in rather low amounts, of from about 0.1 to about 50 pphr.

It has further been contemplated that a substantial increase in the antibacterial and antifungal efficacy may be provided upon washing the finished inventive article. Abrading the surface of such an article may permit increases in such characteristics due to an increase in Ag+ release; however, industrial laundering of certain rubber products (mats, and the like) may provide improved antimicrobial, antifungal, etc., efficacy through a simple washing. In fact, such an increase may steadily improve with greater numbers of consistent washes such that a rubber article, as first vulcanized, may exhibit lower overall antibacterial and antifungal activity than one that has been washed one, two, three, and up to at least 20 times (in a standard industrial rotary washing machine). Such a surprising benefit may permit utilization of such rubber articles as floor coverings (mats, as one example, such as those with carpeted portions or those which are rubber alone; particularly foamed rubber mats for antifatigue properties and reduced specific gravity so as to reduce the chances of machinery damage during such industrial rotary launderings and dryings), and other articles which can be easily washed within standard laundry machines.

Furthermore, as alluded to above, friction with the subject rubber article surface can remove very slight layers of rubber from the article surface thereby permitting "fresh" silver-comprising crystallites at the surface to act as desired in their antibacterial and/or antifungal capacities. Basically, then, the inventive article produced from the inventive raw rubber formulation exhibits an even dispersion of antimicrobial particles throughout the entire rubber article. Such an even dispersion of the biocide throughout the rubber article thus provides a reservoir of fresh crystallites containing the biocidal metallic ion. As layers of the rubber are worn and abraded away, antimicrobial particles containing untapped silver ions become available.

The preferred bisphenol cured fluoroelastomer rubber-containing articles of this invention containing the antimicrobial agent can be processed into rubber articles which exhibit excellent antimicrobial qualities as well as antimicrobial efficiency throughout the rubber article's lifetime. Examples of other such rubber articles encompassed within this invention include, but are not limited to hard rubber mats, static dissipative rubber mats, anti-fatigue rubber mats, rubber mats which include a face fiber, rubber link mats, rubber seals and gaskets, rubber medical goods, rubber gloves, rubber medical devices, rubber conveyor belts, rubber belts and rubber wheels used in food processing, rubber clothing, rubber shoes, rubber boots, rubber tubing, and rubber automotive fuel hoses. Such inventive formulations may also be incorporated into a multilayered rubber article in which the antimicrobial agent can be incorporated into any surface layer and still provide the desired antimicrobial efficiency.

Of particular interest is the formation of multilayered rubber articles wherein at least one of such rubber layer exhibits the desired antimicrobial activity and thus is made from an inventive fluoroelastomer rubber-containing article. Such layered articles may be adhered together through co-vulcanization, gluing, and the like. Furthermore, layers of other types of materials may be placed between the rubber layers as well to provide, as one non-limiting property, better structural stability to the desired multilayered article.

The non-limiting, preferred embodiments of these rubber formulations and articles are discussed in greater detail below.

DESCRIPTION OF THE PREFERRED EMBODIMENTS

Inventive Raw Rubber Formulations

| (INVENTIVE) FLUOROELASTOMER BASE FORMULATION 1 | |
|---|---|
| Component | Amount |
| Fluoroelastomer Rubber (Dai-el G751 from Daikin Industries, Ltd.)* | 100 parts |
| N990 Black (CABOT carbon black filler) | 20 pphr |
| Magnesium oxide | 3 pphr |
| Calcium hydroxide | 6 pphr |
| Antimicrobial (ALPHASAN® RC2000 from Milliken & Company) | 2% by weight |

*Bisphenol added prior to compounding.

| (INVENTIVE) FLUOROELASTOMER BASE FORMULATION 2 | |
|---|---|
| Component | Amount |
| Fluoroelastomer Rubber (Dai-el G902 from Daikin Industries, Ltd.) | 100 parts |
| N990 Black (CABOT carbon black filler) | 20 pphr |
| di-(tert-butyl-peroxy-isopropyl)benzene (14/40 from AKM) | 2 pphr |
| di-(tert-butyl-peroxy-trimethyl)cyclohexane (29/40 from AKM) | 2 pphr |
| Antimicrobial (ALPHASAN® RC2000 from Milliken & Company) | 2% by weight |

These inventive raw rubber formulations were created using ALPHASAN® RC2000 (available from Milliken & Company), a silver ion-exchange zirconium phosphate salt, exhibiting 10% Ag+ concentration and including $Ag_xNa_y$-$H_zZr_2(PO_4)_3$, where $x+y+z=1$, as other components (% by weight).

The compounding of ingredients within each formulation can be carried out in an open mill, an internal mixer, or an extruder where intensive mixing within the polymer matrix of each component will take place. During the mixing operation, the control of temperature rise, due to high shear incorporation of the ingredients, is crucial to ensure that pre-vulcanization (scorch) does not take place during processing. Generally, a maximum temperature of 120° C. is reached on single stage (pass) mixing through an internal mixer. The compounds can be further processed after mixing into specific forms to allow adequate presentation for manufacturing into products. This could be calendering, extrusion, granulation/pelletization, strip form, fabrication and preforming into specific shaped blanks.

The vulcanization of the compounds can be in the form of molding (compression, transfer, injection), continuous extrusion (LCM, UHF[where permissible], autoclave and hot air), and coatings. The vulcanization (cure) temperatures can range from 150° C. to 250° C. In this specific situation, the rubber articles were calendared into rough mat structures and then subjected to vulcanization under high temperature and pressure.

Testing of Vulcanized Rubber Articles

Table 1 illustrates silver-ion extraction (or, silver elution) results from the inventive rubber article. The rubber article was immersed in an aqueous salt extraction solution (sodium phosphate) for 24 hours; the extract was then analyzed by inductively coupled plasma measurements for a measurement of available silver removed from the article surface. The FKM Base Formulation 1 exhibited 1.049 ppb/cm$^2$ and 16.570 ng/cm$^2$ surface available Ag+ ions.

Thus, the inventive article exhibited controlled release of silver ions. As previously discussed, silver elution at a rate of greater than 1.5 ng/cm$^2$ is believed to provide maximum log kill reduction after 24 hours for *S. aureus* when tested in accordance with ATCC Test Method 6538 and for *K. pneumoniae* when tested in accordance with ATCC Test Method 4352. Accordingly, it is believed that the silver elution results shown above provide highly desirable long-term antimicrobial characteristics within the cured rubber article.

Having described the invention in detail, it is obvious that one skilled in the art will be able to make variations and modifications thereto without departing from the scope of the present invention. Accordingly, the scope of the present invention should be determined only by the claims appended hereto.

We claim:

1. A dimensionally stable vulcanized rubber article comprising at least a majority of fluoroelastomer rubber and at least one silver-based antimicrobial compound, wherein said rubber article exhibits silver elution at a rate of at least 1.5 ng/cm$^2$ after 24 hours exposure at room temperature, and wherein said article optionally comprises at least one silver ion release control additive.

2. The rubber article of claim 1 wherein said article exhibits silver elution at a rate of at least 2.5 ng/cm$^2$ after 24 hours exposure at room temperature.

3. The rubber article of claim 1 wherein said silver-based antimicrobial compound is selected from the group consisting of elemental silver, silver oxides, silver salts, silver ion exchange compounds, silver zeolites, silver glasses, and any mixtures thereof.

4. The rubber article of claim 2 wherein said silver-based antimicrobial compound is selected from the group consisting of elemental silver, silver oxides, silver salts, silver ion exchange compounds, silver zeolites, silver glasses, and any mixtures thereof.

5. The rubber article of claim 1 wherein said at least one silver ion control release additive is present.

6. The rubber article of claim 5 wherein said at least one silver ion control release additive is selected from the group consisting of fillers, oils, pigments, salts, antistatic agents, and any mixtures thereof.

7. The rubber article of claim 6 wherein said at least one silver ion control release additive is a filler selected from the group consisting of carbon black, magnesium oxide, calcium hydroxide, and any mixtures thereof.

8. The rubber article of claim 1 wherein said article is a mat structure.

9. A pre-vulcanized rubber formulation comprising at least one rubber constituent, the majority of which must be fluoroelastomer rubber, at least one silver-based antimicrobial compound and at least one curing compound, wherein all of said curing compound present within said formulation does not include an appreciable amount of sulfur-based compounds, and wherein said rubber formulation optionally comprises at least at least one silver ion release control additive.

10. The rubber formulation of claim 9 wherein said silver-based antimicrobial compound is selected from the group consisting of elemental silver, silver oxides, silver salts, silver ion exchange compounds, silver zeolites, silver glasses, and any mixtures thereof.

11. The rubber formulation of claim 9 wherein said curing compound comprises a majority amount by weight of at least one bisphenol.

12. The rubber formulation of claim 10 wherein said curing compound comprises a majority amount by weight of at least one bisphenol.

13. The rubber formulation of claim 9 wherein said curing compound comprises a majority amount by weight of at least one peroxide.

14. The rubber formulation of claim 10 wherein said curing compound comprises a majority amount by weight of at least one peroxide.

15. The rubber formulation of claim 9 wherein said at least one silver ion control release additive is present.

16. The rubber formulation of claim 15 where said at least one silver ion control release additive is selected from the group consisting of fillers, oils, pigments, salts, antistatic agents, and any mixtures thereof.

17. The rubber formulation of claim 16 wherein said at least one silver ion control release additive is a filler selected from the group consisting of carbon black, magnesium oxide, calcium hydroxide, and any mixtures thereof.

18. A method of producing a rubber article exhibiting long-lasting, regenerable antimicrobial characteristics, comprising the steps of compounding together the unvulcanized rubber formulation of claim 9, molding said rubber formulation into a preselected shape, and vulcanizing said rubber formulation under high pressure and exposure to high temperature.

19. A method of producing a rubber article exhibiting long-lasting, regenerable antimicrobial characteristics, comprising the steps of compounding together the unvulcanized rubber formulation of claim 15, molding said rubber formulation into a preselected shape, and vulcanizing said rubber formulation under high pressure and exposure to high temperature.

20. A rubber composition comprising at least one fluoroelastomer rubber component, at least one bisphenol curing agent, and at least one silver-based antimicrobial agent, and optionally comprising at least one silver ion release control additive.

21. A rubber composition comprising at least one fluoroelastomer rubber component, at least one peroxide curing agent, and at least one silver-based antimicrobial agent, and optionally comprising at least one silver ion release control additive.

* * * * *